United States Patent
Saito et al.

(10) Patent No.: US 11,225,619 B2
(45) Date of Patent: Jan. 18, 2022

(54) AVIATION BIOFUEL BASE MATERIAL, AVIATION BIOFUEL INCLUDING SAME, AND METHOD FOR MANUFACTURING AVIATION BIOFUEL

(71) Applicant: IDEMITSU KOSAN CO., LTD., Tokyo (JP)

(72) Inventors: Yasuyo Saito, Tokyo (JP); Akio Imai, Tokyo (JP); Mitsuru Koike, Tokyo (JP); Hiroyuki Tooi, Tokyo (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 0 days.

(21) Appl. No.: 16/756,192

(22) PCT Filed: Oct. 10, 2018

(86) PCT No.: PCT/JP2018/037663
§ 371 (c)(1),
(2) Date: Apr. 15, 2020

(87) PCT Pub. No.: WO2019/078057
PCT Pub. Date: Apr. 25, 2019

(65) Prior Publication Data
US 2021/0189268 A1    Jun. 24, 2021

(30) Foreign Application Priority Data
Oct. 16, 2017 (JP) .............................. JP2017-200095

(51) Int. Cl.
*C10L 1/04* (2006.01)
*C07C 1/22* (2006.01)

(52) U.S. Cl.
CPC ............... *C10L 1/04* (2013.01); *C07C 1/22* (2013.01); *C10L 2200/043* (2013.01); *C10L 2200/0469* (2013.01); *C10L 2270/04* (2013.01); *C10L 2290/24* (2013.01)

(58) Field of Classification Search
CPC ............ C10L 1/04; C10L 2200/0469; C10L 2290/24; C10L 2200/043; C10L 2270/04; C10L 9/16; C07C 1/22; C07C 2527/054; C07C 5/03; C07C 2523/44; C07C 2/84; C07C 2601/16; C10G 2300/308; C10G 2300/302; C10G 2300/304; C10G 2300/1014; C10G 2400/08; C10G 3/44; C10G 3/48; C10G 3/50; C10G 50/00; C10G 2/84; C10G 13/28; C10G 5/03; Y02P 30/20
See application file for complete search history.

(56) References Cited

U.S. PATENT DOCUMENTS

| | | | |
|---|---|---|---|
| 8,193,402 B2 | 6/2012 | Gruber et al. | |
| 9,840,676 B1 * | 12/2017 | Harvey | C10L 1/08 |
| 2006/0199988 A1 * | 9/2006 | Kowalik | C10L 1/04 |
| | | | 585/533 |
| 2009/0299109 A1 * | 12/2009 | Gruber | C10G 50/00 |
| | | | 585/14 |
| 2011/0203253 A1 * | 8/2011 | Derr | C10L 1/08 |
| | | | 60/204 |
| 2011/0288352 A1 | 11/2011 | Peters et al. | |
| 2012/0197032 A1 * | 8/2012 | Firth | C11B 3/04 |
| | | | 554/174 |
| 2012/0238787 A1 * | 9/2012 | Gruber | C12P 5/00 |
| | | | 585/14 |
| 2013/0006012 A1 * | 1/2013 | Firth | C11C 3/003 |
| | | | 560/218 |

FOREIGN PATENT DOCUMENTS

| | | | |
|---|---|---|---|
| JP | 2011505490 A | | 2/2011 |
| JP | 2015113405 A | * | 6/2015 |
| JP | 2016033129 A | | 3/2016 |

OTHER PUBLICATIONS

ASTM D1655 Standard Specification for Aviation Turbine Fuels (Year: 2020).*
International Search Report for PCT/JP2018/0737663 dated Dec. 20, 2018.
English Abstractor JP2016033129, Publication Date: Mar. 10, 2016.

* cited by examiner

*Primary Examiner* — Pamela H Weiss
(74) *Attorney, Agent, or Firm* — Millen White Zelano and Branigan, PC; Csaba Henter

(57) ABSTRACT

An aviation biofuel component including 90.0 vol % or more of isoparaffins of C10 to C12 and 30.0 vol % or more of isoparaffins which are at least C10 or C12.

7 Claims, No Drawings

AVIATION BIOFUEL BASE MATERIAL, AVIATION BIOFUEL INCLUDING SAME, AND METHOD FOR MANUFACTURING AVIATION BIOFUEL

TECHNICAL FIELD

The present invention relates to an aviation biofuel component including an isoparaffin derived from a biomass including hemicellulose or cellulose, an aviation biofuel including the component, and a method for producing the aviation biofuel.

BACKGROUND ART

At present, as awareness of the environment increases, introduction of fuels produced by using plants as raw materials, so-called biofuels, is required. These biofuels meet GHG (greenhouse effect gas) emissions standards, while there is concern that they will compete with food production if the raw materials are from edible parts of crops such as corn and sugar cane.

Research is therefore underway to produce biofuels that do not compete with food production. For example, Patent Literature 1 describes a gasoline composition including cellulose-derived materials, constituting non-eating parts such as stems and leaves that are normally discarded and satisfying the properties required for use in gasoline engines. The gasoline composition is mainly used in vehicles.

CITATION LIST

Patent Literature

Japanese Patent Application Laid-Open No. 2017-19950

SUMMARY OF THE INVENTION

Technical Problem

The introduction of biofuels is not limited to fuels for vehicles, but is also required for fuels for aircraft, so-called jet fuels. However, in an environment at several thousand meters of altitude where jet fuel is used, the temperature, air pressure, and air density are lower than the ground surface, and the required fuel performance is different from that of the ground surface where fuel for vehicles is used. Specifically, it is necessary to satisfy performance such as a low freezing point, excellent combustibility, and a predetermined flash point from the viewpoint of safety and the like.

It is therefore an object of the present invention to provide an aviation biofuel component for producing an aviation biofuel having a low freezing point, excellent combustibility, and a predetermined flash point, an aviation biofuel including the same, and a method for producing an aviation biofuel having a low freezing point, excellent combustibility, and a predetermined flash point.

Solution to Problems

In order to achieve these objectives, the inventors have conducted extensive research and found that by dimerizing one or more olefins selected from the group consisting of pentene derived from biomass including hemicellulose and hexene derived from biomass including cellulose to make isoparaffins of C10 to C12, those isoparaffins can be used as aviation biofuel component. That is, the present invention is an aviation biofuel component including 90.0 vol % or more of isoparaffins of C10 to C12 and 30.0 vol % or more of isoparaffins which are at least one of C10 or C12.

The present invention also provides an aviation biofuel including 1.0 to 40.0 vol % of the aviation biofuel component.

Further, the present invention is a method of manufacturing an aviation biofuel, comprising blending an aviation biofuel component with other components, where the aviation biofuel component including at least 90.0 vol % or more of isoparaffins of C10 to C12 and at least 30.0 vol % or more of isoparaffins which are at least C10 or C12, the isoparaffins being obtained by dimerizing one or more olefins selected from the group consisting of pentene derived from biomass including hemicellulose and hexene derived from biomass including cellulose.

Advantageous Effects of Invention

According to the present invention, it is possible to provide an aviation biofuel component with a low freezing point, excellent combustibility, and a predetermined flash point for producing an aviation biofuel, an aviation biofuel including the component, and a method for producing an aviation biofuel with a low freezing point, excellent combustibility, and a predetermined flash point.

DESCRIPTION OF EMBODIMENTS

<Aviation Biofuel Component>

An aviation biofuel component according to the present invention comprises isoparaffins of C10 to C12 derived from biomass including hemicellulose or cellulose, preferably. The isoparaffins of C10 to C12 derived from hemicellulose or cellulose are produced from hemicellulose or cellulose included in lignocellulosic biomass. Lignocellulosic biomass is a biomass composed primarily of cellulose, hemicellulose, and lignin. Such lignocellulosic biomass also includes agricultural and forestry resources such as hardwood, softwood, rice straw, straw, rice husk, corn stover, bagasse, and their wastes; energy crops such as switchgrass, erianthus, nepiagrass, and pampas grass; wood chips derived therefrom; wood debris; pulp; and wastepaper. Lignocellulosic biomass is a plant-derived resource that does not compete with food production and does not cause food problems.

The isoparaffins of C10 to C12 derived from biomass including hemicellulose or cellulose account for 90.0 vol % or more, preferably 92.0 vol % or more, and more preferably 94.0 vol % or more in the aviation biofuel component. From the viewpoint of the effective utilization of biomass, the higher the content of isoparaffins of C10 to C12 derived from biomass including hemicellulose or cellulose, the better.

The aviation biofuel component according to the present invention contains 30.0 vol % or more of isoparaffin of C10 derived from biomass including hemicellulose (hereinafter referred to as isoparaffin of C10) or isoparaffin of C12 derived from biomass including cellulose (hereinafter referred to as isoparaffin of C12). That is, the aviation biofuel component may contain 30.0 vol % or more of isoparaffin of C10, or 30.0 vol % or more of isoparaffin of C12. The aviation biofuel component may contain 30.0 vol % or more of isoparaffins of C10 and 30.0 vol % or more of isoparaffins of C12.

Dimerization of pentenes from biomass including hemicellulose leads to the production of isoparaffin of C10, and hence the proportion of isoparaffin of C10 increases. When more hemicellulose is used as a raw material, the aviation biofuel component preferably contains 40.0 vol % or more of isoparaffin of C10, more preferably 60.0 vol % or more of isoparaffin of C10, and still more preferably 80.0 vol % or more of isoparaffin of C10. In this case, for example, 40.0 to 70.0 vol % of isoparaffin of C10, 20.0 to 40.0 vol % of isoparaffin of C11 derived from biomass including hemicellulose and cellulose (hereinafter referred to as isoparaffin of C11), and 5.0 to 25.0 vol % of isoparaffin of C12 can be used.

Dimerization of hexene from biomass including cellulose leads to the production of isoparaffin of C12, and hence the proportion of isoparaffin of C12 increases. When more cellulose is used as the raw material, the aviation biofuel component preferably contains 40.0 vol % or more of isoparaffin of C12, more preferably 60.0 vol % or more, still more preferably 80.0 vol % or more, and particularly preferably 90.0 vol % or more. In this case, for example, 5.0 to 25.0 vol % of isoparaffin of C10, 20.0 to 40.0 vol % of isoparaffin of C11, and 40.0 to 70.0 vol % of isoparaffin of C12 can be used.

In addition to the isoparaffins of C10 to C12 derived from biomass including hemicellulose or cellulose, the aviation biofuel component according to the present invention may also contain isoparaffins of C15 to C18 obtained by trimerizing pentene and/or hexene. The isoparaffins of C 15 to C18 may account for, for example, 1.0 to 10.0 vol %, preferably 2.0 to 8.0 vol %, in the aviation biofuel component.

The aviation biofuel component according to the present invention preferably has a density (15° C.) of 0.730 to 0.778 g/cm$^3$. The kinematic viscosity (−20° C.) is preferably 8.0 mm$^2$/s or less. The freezing point is preferably −40° C. or less, more preferably −47° C. or less. The smoke point is preferably 18 mm or more, more preferably 20 mm or more, still more preferably 25 mm or more, and most preferably 30 mm or more. The aromatics is preferably 5.0 vol % or less, and the sulfur is preferably 10 mass ppm or less.

<Aviation Biofuel>

The aviation biofuel according to the present invention desirably contains 1.0 to 40.0 vol %, preferably 5.0 to 40.0 vol %, more preferably 10.0 to 40.0 vol %, more preferably 15.0 to 40.0 vol %, particularly preferably 20.0 to 35.0 vol %, and most preferably 25.0 to 30.0 vol % of the aviation biofuel component according to the present invention. When the content of the aviation biofuel component is small, the content of hemicellulose, cellulose, and the like derived from plants becomes small, and the effect of reducing the amount of carbon dioxide emissions becomes small. If the content of the aviation biofuel component is too large, the properties as a jet fuel may not be satisfied.

The aviation biofuel according to the present invention satisfies the properties necessary for a jet fuel including the properties described below, even if the aviation biofuel contains the aviation biofuel component according to the present invention, that is, the aviation biofuel contains 90.0 vol % or more of isoparaffins of C10 to C12 and 30.0 vol % or more of isoparaffins which are at least C10 or C12.

The aviation biofuel according to the present invention preferably have densities of from 0.775 to 0.840 g/cm$^3$, more preferably from 0.775 to 0.800 g/cm$^3$. If the density is too low, the fuel mileage may be deteriorated, and if the density is too high, the combustibility may be deteriorated.

The kinematic viscosity (−20° C.) is preferably 8.0 mm$^2$/s or less, more preferably 7.0 mm$^2$/s or less. If the kinematic viscosity is high, the fuel spray state in the turbine may be deteriorated and good combustibility may not be maintained.

The freezing point is preferably 40° C. or less, more preferably 47° C. or less. It is preferable that the freezing point is low enough to prevent the wax in the fuel from precipitating in an environment in which the aircraft flies.

The smoke point is preferably 18 mm or more, more preferably 20 mm or more, and even more preferably 25 mm or more. When the smoke point is low, the combustibility is deteriorated.

The flash point is preferably 38° C. or more, more preferably 40° C. or more. When the flash point is low, fire hazard during storage and in use increases.

It is preferable that the aviation biofuel according to the present invention meets the Jet A standard of the ASTM, and more preferable that the aviation biofuel meets the Jet A-1 standard.

<Aviation Biofuel Production Method>

The method for producing an aviation biofuel according to the present invention includes a step of producing an aviation biofuel component and a step of blending the produced aviation biofuel component with another component.

The aviation biofuel component can be obtained by dimerizing one or more olefins selected from the group consisting of pentene derived from biomass including hemicellulose and hexene derived from biomass including cellulose, and followed by hydrogenating those dimmers.

The pentene derived from hemicellulose can be obtained, for example, by producing pentanol from hemicellulose contained in lignocellulosic biomass and then dehydrating the produced pentanol derived from hemicellulose. Pentanol from hemicellulose can be efficiently obtained in a single reactor vessel by hydrolysis of hemicellulose to sugars in an aqueous phase and hydrogenolysis of the sugars in the presence of Ir—Re (iridium-rhenium) based catalysts and at temperatures at which hemicellulose is decomposed, and followed by adding an oil phase consisting of a liquid hydrocarbon, and dissolving pentanol in the oil phase. (Japanese Patent Application Laid-Open No. 2016-33129)

The Ir—Re based catalysts are based on Ir and Re and are not particularly limited, but Ir-ReOx/SiO$_2$ can increase the conversion of hemicellulose and the yield of pentanol. Where x in ReOx represents the number of oxides and is any real number. Particularly, when Ir-ReOx/SiO$_2$ is used, the molar ratio of Re to Ir is 1 or more, so that pentanol can be obtained in a higher yield, which is preferable.

As the oil phase, for example, a saturated hydrocarbon such as normal paraffin, isoparaffin, cycloparaffin, or the like, or an aromatic hydrocarbon is preferable.

The oil phase is not to interfere with the reactions in the hydrolysis and hydrogenolysis steps described above. For example, when ether is used as a solvent, the ether itself is decomposed, so that the function to dissolve an alcohol as an oil phase may be impaired. In addition, an alcohol or the like having an OH group is adsorbed on the catalyst to cover the active site, which may impair the catalytic performance. In addition, unsaturated hydrocarbons, such as olefinic hydrocarbons, are themselves hydrogenated, consuming the hydrogen used in the hydrogenation of xylose and the hydrogenolysis of xylitol, and hence reducing the yield of pentanol. The aromatic hydrocarbon can also be hydrogenated, but since the reaction rate of such hydrogenation is slow, it can also be used as a solvent.

The oil phase needs to be a liquid phase (fluid) at the temperatures and pressures at which the Ir—Re based catalysts react. Typically, since the reaction conditions of the catalyst are 140° C. to 200° C. and 1 MPa to 10 MPa, the boiling point of the solvent is 140° C. or more in 1 MPa, preferably 200° C. or more in 1 MPa, and more preferably 290° C. or more. In addition, since recovery of alcohol becomes difficult if the oil phase becomes a solid phase when the oil phase is taken out, it is preferable to maintain the liquid phase even at normal temperature and normal pressure. As such a saturated hydrocarbon, for example, n-dodecane, n-decane, or the like can be used. Note that two or more kinds of oil phases may be mixed and used.

Others in the method for producing pentanols from hemicelluloses are described, for example, in Sibao Liu et al., Green Chem., 2016, 18, 165-175.

Pentanol can be converted to pentene by a known acid-catalyzed dehydration reaction. The pentenes obtained include 1-pentene and 2-pentene. In pentenes derived from hemicelluloses, the amount of 1-pentene is preferably from 5.0 to 15.0 vol %, more preferably from 7.0 to 13.0 vol %. The amount of 2-pentene is preferably 85.0 to 95.0 vol %, more preferably 87.0 to 93.0 vol %. In addition, 1-pentene and 2-pentene may be fractionated by a precision distillation operation.

The hexene derived from cellulose can be obtained, for example, by producing hexanol from cellulose included in lignocellulosic biomass and dehydrating the produced hexanol derived from cellulose. Hexanol can be efficiently obtained in a single reactor vessel by hydrolysis cellulose to sugars in an aqueous phase, and hydrogenolysis of the sugars in the presence of Ir—Re (iridium-rhenium) based catalysts and at temperatures at which cellulose is decomposed, and followed by adding an oil phase consisting of a liquid hydrocarbon, and dissolving hexanol in the oil phase. (Japanese Patent Application Laid-Open No. 2016-33129). The catalyst and the oil phase may be the same as those described in the above-mentioned method for producing pentene derived from hemicellulose. Others in the method for producing hexanol from cellulose are described, for example, in Sibao Liu et al., ChemSusChem, 2015, 8, 628-635. Hexanol can be converted to hexene by a known acid-catalyzed dehydration reaction. The resulting hexenes include 1-hexene, 2-hexene, and 3-hexene. In the hexene derived from cellulose, the amount of 1-hexene is preferably 1.0 to 15.0 vol %, more preferably 3.0 to 9.0 vol %, and more preferably 3.0 to 7.0 vol %. Preferably, the amount of 2-hexene is from 55.0 to 80.0 vol %, more preferably from 60.0 to 75.0 vol %, and even more preferably from 60.0 to 70.0 vol %. Preferably, the amount of 3-hexene is from 10.0 to 40.0 vol %, more preferably from 19.0 to 28.0 vol %, and even more preferably from 20.0 to 28.0 vol %. In addition, 1-hexene, 2-hexene, and 3-hexene may be fractionated by a precision distillation operation.

Hemicellulose-derived pentenes and cellulose-derived hexenes may be produced separately from lignocellulosic biomass in separate reaction vessels, or hemicellulose-derived pentenes and cellulose-derived hexenes may be produced from lignocellulosic biomass in the same reaction vessel.

The dimerization of pentenes derived from biomass including hemicellulose can be carried out by a known acid-catalyzed polymerization reaction. Dimerization of the pentene gives an olefin of C10. The dimerization of hexene derived from biomass including cellulose can be carried out by a known acid-catalyzed polymerization reaction. Dimerization of hexene gives an olefin of C12. It is also possible to dimerize pentene and hexene simultaneously. Simultaneous dimerization also gives an olefin of C11. Upon dimerization, a trimer may be formed.

There is one double bond in the resulting dimer molecule. Hydrogenation of these over known hydrogenation catalysts under hydrogen pressure produces isoparaffins of C10 to C12. Hydrogenation of the trimer also produces isoparaffins of C15 to C18. The composition thus obtained contains 90.0 vol % or more, preferably 92.0 vol % or more, more preferably 94.0 vol % or more of isoparaffins of C10 to C12.

The resulting isoparaffins of C10 to C12, derived from biomass including hemicellulose or cellulose can be used as the aviation biofuel component according to the present invention described above.

Next, the obtained aviation biofuel component and another component are blended. The other component preferably meets the Jet A standard of the ASTM, and more preferably meets the Jet A-1 standard. The aviation biofuel component is desirably 1.0 to 40.0 vol %, preferably 5.0 to 40.0 vol %, more preferably 10.0 to 40.0 vol %, more preferably 15.0 to 40.0 vol %, particularly preferably 20.0 to 35.0 vol %, and most preferably 25.0 to 30.0 vol % in the aviation biofuel.

The aviation biofuel produced as described above can be used as the aviation biofuel according to the present invention described above.

EXAMPLES

Synthesis Example 1: Preparation of Hemicellulose-Derived Pentene

[Preparation of Catalysts, Etc.]

An aqueous solution of iridium chloride ($H_2IrCl_6$) or an aqueous solution of iridium nitrate was added dropwise to silicon dioxide ($SiO_2$) (CARiACT G-6 manufactured by Fuji Silysia Chemical Ltd.), and the whole was wetted and dried at about 90° C. The wetting and drying process was repeated so that Ir was 4% by mass with respect to the entire catalyst. Further, drying was performed at 110° C. for about half a day. The same wetting and drying steps were then repeated with an aqueous solution of ammonium perrhenate ($NH_4ReO$) to be supported by the silicon dioxide so that the molar ratio of Re to Ir, i.e. [Re]/[Ir], was between 0.25 and 3. Thereafter, the catalyst was calcined at 500° C. for 3 hours to obtain a Ir-ReOx/$SiO_2$ catalyst.

As the reaction vessel, an autoclave having an inner tube made of glass was used. An electric furnace was equipped around the reaction vessel so that the inside of the reaction vessel could be heated. In order to stir the inside of the tube, the reaction vessel was placed on a magnetic stirrer and a magnetic stirrer tip (stirrer) coated with Teflon® was put into the inner tube of the reaction vessel. 1.0 parts by weight of the above Ir-ReOx/$SiO_2$ catalysts and 63.3 parts by weight of water were put in a reactor, and hydrogen-substitution was repeated three or more times. Hydrogen was introduced so as to become 8 MPa in the total pressure when the inside of the reactor reached 200° C., and the catalyst was reduced at 200° C. for 1 hour.

[Production of Pentanol]

Xylan, which is a main component of hemicellulose, was subjected to a mill treatment in advance. In such a mill treatment, 100 $ZrO_2$ balls together with xylan were put into the drums of the ball mill, and grinding was performed for 2 hours at a rotational speed of 300 rpm. It should be noted that the obtained xylan is sufficiently ground by grinding for 2 hours or more.

3.3 parts by weight of the above milled xylan was added to the reaction vessel subjected to the reduction treatment of the catalyst as described above. In the reactor, 20.0 to 100.0 parts by weight of n-dodecane was added as an oil phase, hydrogen was introduced so as to become 6 MPa at room temperature, and inside of the reactor was held at 140° C. for 144 hours to obtain pentanol derived from hemicellulose.

[Production of Pentene]

1.0 parts by weight of pentanol derived from hemicellulose including at least one of 1-pentanol, 2-pentanol and 3-pentanol obtained in the above manner was introduced into another reaction vessel (the same type as the autoclave described above), 10.0 parts by weight of tridecane as a solvent, and 0.2 parts by weight of zeolite (HZSM-5) as an acid-catalyst were added, and then, nitrogen was introduced so as to become 0.6 MPa at room temperature, and then this reaction vessel was raised to a predetermined reaction temperature of 180° C. in about 20 minutes. The dehydrated reaction product immediately after reaching the reaction temperature was analyzed. As a result, hemicellulose-derived pentenes including 1-pentene and 2-pentene were obtained.

Synthesis Example 2: Preparation of Hexene Derived from Cellulose

[Preparation of Catalysts, Etc.]

A catalyst or the like was prepared in the same manner as in Synthesis Example 1.

[Production of Hexanol]

Cellulose derived from lignocellulosic biomass was milled in advance. In such a mill treatment, 100 $ZrO_2$ balls together with cellulose were put into drums of a ball mill, and grinding was performed at a rotational speed of 300 rpm for 2 hours. If the cellulose is ground for 2 hours or more, the cellulose obtained is sufficiently ground.

3.3 parts by weight of the cellulose subjected to the mill treatment was added to the reaction vessel subjected to the reduction treatment of the catalyst as described above. In the reactor, 20.0 to 100.0 parts by weight of n-dodecane was added as an oil phase, hydrogen was introduced so as to be a 6 MPa at room temperature, and the inside of the reactor was held at 190° C. for 24 hours to obtain cellulose-derived hexanols.

[Production of Hexene]

1.0 parts by weight of cellulose-derived hexanol including at least one of 1-hexanol, 2-hexanol, and 3-hexanol obtained in the above manner was introduced into another reaction vessel (same type as the autoclave described above), 10.0 parts by weight of tridecane as a solvent, and 0.2 parts by weight of zeolite (HZSM-5) as an acid catalyst were added, and then nitrogen was introduced so as to become 0.6 MPa at room temperature, and the reaction temperature was raised to 180° C. in about 20 minutes. The dehydrated reaction product immediately after reaching the reaction temperature was analyzed. As a result, cellulose-derived hexenes including 1-hexene, 2-hexene, and 3-hexene was obtained.

Synthetic Example 3: Simultaneous Production of Hexene from Hemicellulose and Pentene from Cellulose

[Preparation of Catalysts, Etc.]

A catalyst or the like was prepared in the same manner as in Synthesis Example 1.

[Preparation of Pentanol and Hexanol]

Xylan, which is a main component of hemicellulose derived from lignocellulosic biomass, and cellulose derived from lignocellulosic biomass were subjected to mill treatment in advance. In such a mill treatment, 100 $ZrO_2$ balls together with xylanes and celluloses were put into drums of a ball mill, and grinding was performed for 2 hours at a rotational speed of 300 rpms. It should be noted that, if grinding is performed for 2 hours or more, the obtained xylan and cellulose are sufficiently ground.

3.3 parts by weight of the milled xylan and cellulose were added to the reaction vessel subjected to the reduction treatment of the catalyst as described above. In the reactor, 20.0 to 100.0 parts by weight of n-dodecane was added as an oil phase, hydrogen was introduced so as to become 6 MPa at room temperature, and the inside of the reactor was kept at 190° C. for 24 hours to obtain pentanol derived from hemicellulose and hexanol derived from cellulose.

[Production of Pentene and Hexene]

1.0 parts by weight of hemicellulose-derived pentanol including at least one of 1-pentanol, 2-pentanol, and 3-pentanol and cellulose-derived hexanol including at least one of 1-hexanol, 2-hexanol, and 3-hexanol obtained in the above manner were introduced into another reaction vessel (the same type as the autoclave described above), 10.0 parts by weight of tridecane as a solvent, and 0.2 parts by weight of zeolite (HZSM-5) as an acid catalyst were added, and then nitrogen was introduced so as to become 0.6 MPa at room temperature, and the reaction temperature was raised to 180° C. in about 20 minutes. The dehydrated reaction product immediately after reaching the reaction temperature was analyzed. As a result, hemicellulose-derived pentene including 1-pentene and 2-pentene and hemicellulose-derived hexene including 1-hexene, 2-hexene, and 3-hexene were obtained.

Synthesis as described above yields pentene and hexene with the following isomer ratios in pentenes and hexenes, as described in Table 1.

TABLE 1

| (Vol %) | | Sample A | Sample B | | Sample C | |
|---|---|---|---|---|---|---|
| Pentenes | 1-pentene | 54.4 | 4.9 | 100 | 9.1 | |
| | 2-pentene | | 49.5 | | 90.9 | |
| Hexenes | 1-hexene | 45.6 | 3.0 | | | 100 | 6.7 |
| | 2-hexene | | 30.4 | | | 66.7 |
| | 3-hexene | | 12.1 | | | 26.7 |

Example 1

1-hexene and an ion-exchange resin (Amberlyst15) (dried overnight at 110° C.), which is an acid catalyst, were introduced into a reaction vessel (300 ml autoclave), nitrogen was introduced into the reaction vessel so as to become 2 MPa at room temperature, and then the temperature was raised to a predetermined reaction temperature of 100° C. in about 20 minutes. Dimerization was carried out by holding for 18 hours after reaching the reaction temperature. After the dimerized reaction solution was taken out, the reaction solution and the hydrogenation catalyst $Pd/SiO_2$ (subjected to reduction treatment; reduction condition: pressure ($H_2$)=5 MPa, temperature=100° C., time=1 h) were put into another reaction vessel (300 ml autoclave) together with an ethanol solvent, then hydrogen was introduced so as to become 5 MPa at room temperature, the inside of the reactor was heated to 30 to 75° C., and held for 2 hours, thereby obtaining an aviation biofuel component according to Example 1. The composition analysis of the obtained component was performed by gas chromatography, and as a result, the isoparaffin of C12 was 91.2 vol % and the isoparaffin of C18 was 8.8 vol %. The density (15° C.) was 0.7759 g/cm³, and the kinematic viscosity (−20° C.) was 6.448 mm²/s, which are measured by the methods described after.

Example 2

30.0 parts by volume of the aviation biofuel component according to Example 1 and 70.0 parts by volume of the component A, which meets the Jet A-1 standard of the ASTM described in Table 2 were blended to obtain an aviation biofuel for Example 2. The properties of the obtained aviation biofuel are shown in Table 2. The properties and the like shown in Table 2 were measured by the following methods.

Density:
Measurements were made according to the JIS K 2249 "Crude Oil and Petroleum Products-Density Test Methods and Density-Weight-Volume Tables".

Kinematic viscosity:
Measurements were made according to the JIS K 2283 "Crude Oil and Petroleum Products-Kinetic Viscosity Test Methods and Viscosity Index Calculation Methods".

Freezing point:
Measured according to JIS K 2276 "Freezing Point Test Methods (Aviation Fuels)".

Smoke Points:
Measurements were made according to the JIS K 2537.

Flash point:
Measurements were made according to JIS K 2265 1.

TABLE 2

|  | Unit | Component A | Example 2 |
| --- | --- | --- | --- |
| Density (15° C.) | g/cm³ | 0.7924 | 0.7875 |
| Kinematic viscosity (−20° C.) | mm²/s | 3.718 | 4.314 |
| Freezing point | ° C. | −49.5 | −54.0 |
| Smoke Points | mm | 24.0 | 27.9 |
| Flash point | ° C. | 43.5 | 47.0 |

The invention claimed is:

1. An aviation biofuel component comprising 90.0 vol % or more of isoparaffins of C10 to C12 and additionally contains isoparaffins of C15 or C18, and does not contain aromatics.

2. The aviation biofuel component of claim 1, comprising 40.0 vol % or more isoparaffin of C12.

3. The aviation biofuel component of claim 1, comprising 40.0 vol % or more isoparaffin of C10.

4. The aviation biofuel component of claim 1, which contains the isoparaffin of C15, which is a trimer of pentene.

5. The aviation biofuel component of claim 1, which contains the isoparaffin of C18, which is a trimer of hexene.

6. The aviation biofuel component of claim 1, which contains 1.0 to 10.0 vol % isoparaffins of C15 or C18.

7. The aviation biofuel component of claim 1, which contains 2.0 to 8.0 vol % isoparaffins of C15 or C18.

\* \* \* \* \*